United States Patent
Wolter et al.

(10) Patent No.: US 10,782,985 B2
(45) Date of Patent: Sep. 22, 2020

(54) USER ASSISTANCE SYSTEM OF A REPROCESSING APPARATUS

(71) Applicant: OLYMPUS WINTER & IBE GMBH, Hamburg (DE)

(72) Inventors: Michael Wolter, Hamburg (DE); Uwe Schoeler, Hoisdorf (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 403 days.

(21) Appl. No.: 15/689,019

(22) Filed: Aug. 29, 2017

(65) Prior Publication Data

US 2018/0011722 A1 Jan. 11, 2018

Related U.S. Application Data

(63) Continuation of application No. PCT/EP2016/053513, filed on Feb. 19, 2016.

(30) Foreign Application Priority Data

Mar. 4, 2015 (DE) ........................ 10 2015 203 850

(51) Int. Cl.
*A61L 2/24* (2006.01)
*G06F 9/451* (2018.01)
(Continued)

(52) U.S. Cl.
CPC .......... *G06F 9/453* (2018.02); *A61B 1/00045* (2013.01); *A61B 1/123* (2013.01);
(Continued)

(58) Field of Classification Search
CPC .................................................. A61L 2202/24
See application file for complete search history.

(56) References Cited

U.S. PATENT DOCUMENTS 9,585,539 B2  3/2017  Dirschus et al.

FOREIGN PATENT DOCUMENTS

DE        19749869 A1   6/1999
DE     202007000934 U1  4/2007
(Continued)

OTHER PUBLICATIONS

Hermann et al. DE 102013100142. Nov. 13, 2014. English machine translation. (Year: 2014).*

(Continued)

*Primary Examiner* — Donald R Spamer
(74) *Attorney, Agent, or Firm* — Scully Scott Murphy & Presser

(57) ABSTRACT

A user assistance system of a reprocessing apparatus for cleaning and disinfecting at least one surgical instrument arranged in a cleaning basket, the user assistance system including: at least one electronically controlled display device; and a controller coupled with the at least one electronically controlled display device, the at least one electronically controlled display device being integrated in a loading station and being configured for arranging the cleaning basket on one side of the display device during the loading of the cleaning basket, the controller being configured to control the display device such that image information is displayed in an actual size and position which indicates a predetermined arrangement within the cleaning basket of the surgical instrument that is to be reprocessed.

13 Claims, 3 Drawing Sheets

(51) Int. Cl.

| | | |
|---|---|---|
| *A61B 1/12* | (2006.01) | |
| *A61B 90/70* | (2016.01) | |
| *A61B 50/10* | (2016.01) | |
| *A61B 90/90* | (2016.01) | |
| *G06F 19/00* | (2018.01) | |
| *A61B 1/00* | (2006.01) | |
| *A61B 50/33* | (2016.01) | |
| *A61B 50/15* | (2016.01) | |
| *G05B 23/02* | (2006.01) | |
| *G16H 40/20* | (2018.01) | |
| *A61B 90/00* | (2016.01) | |
| *A61B 50/34* | (2016.01) | |
| *A61B 17/00* | (2006.01) | |
| *A61B 34/00* | (2016.01) | |
| *A61B 50/18* | (2016.01) | |

(52) U.S. Cl.
CPC .............. *A61B 50/10* (2016.02); *A61B 50/15* (2016.02); *A61B 50/33* (2016.02); *A61B 90/70* (2016.02); *A61B 90/90* (2016.02); *G05B 23/0216* (2013.01); *G06F 19/321* (2013.01); *A61B 1/00006* (2013.01); *A61B 50/34* (2016.02); *A61B 2017/00207* (2013.01); *A61B 2034/252* (2016.02); *A61B 2050/185* (2016.02); *A61B 2090/0811* (2016.02); *A61B 2090/0813* (2016.02); *A61B 2090/701* (2016.02); *A61L 2202/14* (2013.01); *A61L 2202/17* (2013.01); *A61L 2202/24* (2013.01); *G06F 19/325* (2013.01); *G16H 40/20* (2018.01)

(56) References Cited

FOREIGN PATENT DOCUMENTS

| DE | 102013100142 A1 | 7/2014 |
|---|---|---|
| JP | 2007-301128 A | 11/2007 |
| JP | 2013-106790 A | 6/2013 |
| WO | WO 2013/167268 A1 | 11/2013 |

OTHER PUBLICATIONS

Harada et al. JP 2013-106790. Jun. 6, 2013. English machine translation. (Year: 2013).*

Nakajima et al. JP 2007-301128. Nov. 22, 2007. English machine translation. (Year: 2007).*

International Search Report dated May 10, 2016 issued in PCT/EP2016/053513.

* cited by examiner

USER ASSISTANCE SYSTEM OF A REPROCESSING APPARATUS

CROSS-REFERENCE TO RELATED APPLICATION

The present application is a continuation of PCT/EP2016/053513 filed on Feb. 19, 2016, which is based upon and claims the benefit to DE 10 2015 203 850.5 filed on Mar. 4, 2015, the entire contents of each of which are incorporated herein by reference.

BACKGROUND

Field

The present application relates to a user assistance system of a reprocessing apparatus for cleaning and disinfecting at least one surgical instrument that is arranged in a cleaning basket. The present application further relates to a reprocessing apparatus with at least one cleaning basket, a loading station and a user assistance system as well as a medical workstation with a reprocessing apparatus. The present application still further relates to a method for cleaning and disinfecting a surgical instrument and to a computer program product.

Prior Art

High demands are placed on the reprocessing, i.e. the cleaning and disinfection, of surgical instruments. A successful reprocessing requires the surgical instrument, such as an endoscope, to be inserted into the reprocessing apparatus in accordance with the manufacturer specifications and clinical guidelines and, if necessary, connected to the available connectors.

The variety of surgical instruments utilized in the clinical setting requires people charged with the reprocessing to have extensive knowledge. For instance, different types of endoscopes must be inserted into the associated cleaning baskets of the reprocessing apparatus in different ways. An example of a suitable reprocessing apparatus is known under the name ETD, produced by Olympus Winter & Ibe GmbH, Hamburg.

The cleaning basket should be understood to be both a wire basket and a plastic basket, also called a plastic tray, which is designed to accommodate a surgical instrument while it is being reprocessed.

To support the person charged with the cleaning, the various connectors and insertion positions are described in detail in a user handbook for the reprocessing apparatus. Moreover, removable stencils are known, on which the arrangement of the surgical instrument in an associated cleaning basket is portrayed. In light of the large number of different individual components of which a surgical instrument is frequently constructed, however, this process can become very complex. Since many different surgical instruments are used in everyday clinical practice, a learning effect does not really set in for the people responsible for preparing them. The arrangement of the surgical instruments to be reprocessed is relevant to safety and is accordingly subjected to specifications that are updated on a daily basis.

SUMMARY

It is an object to indicate a user assistance system for a reprocessing apparatus as well as a reprocessing apparatus, a medical workplace, a method for cleaning and disinfecting a surgical instrument and a computer program product, the intention being to make it safer and simpler to operate said reprocessing apparatus.

Such object can be solved by a user assistance system of a reprocessing apparatus for cleaning and disinfecting at least one surgical instrument arranged in a cleaning basket, the user assistance system being developed in that it includes at least one electronically controlled display device and a control unit that is coupled with it, the display device being integrated into a loading station and being configured to arrange the cleaning basket on one side of the display device during the loading of the cleaning basket, and the control unit being configured to control the display device such that image information is displayed in the actual size and position, which indicates a predetermined arrangement of the surgical instrument to be reprocessed within the reprocessing basket.

The surgical instrument is e.g. an endoscope, forceps, a clamp or a retractor.

The image information displayed in the actual size and position can be a realistic representation or else an outline of the surgical instrument that is arranged in the cleaning basket. For example, a realistic or nearly realistic image of an endoscope, forceps, etc. can be displayed in the arrangement in which it is has been correctly placed in the cleaning basket. In other words, a representation of the at least one surgical instrument can be represented in an image scale of 1:1, i.e. actual size, with the aid of the electronically controlled display device.

The user of the reprocessing apparatus can get intuitive and easily understandable operating instructions, on the basis of which the at least one surgical instrument can be safely and correctly inserted into the cleaning basket. A graphical representation of the predetermined arrangement of the surgical instrument in the cleaning basket can be understood easily and quickly beyond language barriers. The user assistance system can be adapted to different linguistic and cultural environments.

Moreover, the user assistance system can optimize a loading of the cleaning basket. In addition to the correct arrangement of the at least one surgical instrument, it is provided that multiple surgical instruments can be represented in an at least approximately realistic way, and their optimal arrangement in the cleaning basket with regard to a maximum efficiency of the reprocessing apparatus is displayed. In other words, as many surgical instruments as possible can be arranged in the cleaning basket and are cleaned and disinfected in a reprocessing process, this optimization being undertaken while maintaining strict standards of safety and hygiene for the reprocessing. In this way, the costs of reprocessing the individual surgical instruments are lowered while the high level of safety remains unchanged, since the reprocessing apparatus is optimally employed.

The display device can comprise a flat display that is integrated in the working surface of the loading station, where the working surface can be configured for the placement of the cleaning basket during a loading process. In other words, the display can be located below the cleaning basket during the loading process so that the image information shown on the display can easily be seen by the user during the loading of the cleaning basket.

A first and a second flat display can be provided as a display device and can be coupled to the control unit, the control unit also being configured to display, on the first display, first image information that relates to a top view in the direction of the first display and to display, on the second display, second image information that relates to a side view in the direction of the second display, and in particular the first display and the second display including an angle of at least approximately 90° to each other.

With respect to the aforementioned directions and the angle, reference is always made to an active side of the first or respectively second display. In other words, the top view is in the direction of an active side of the first display, on which the image information is shown. The same applies to the second display. An active side of the display is that side on which the image information is shown.

Image information can be shown in top view on the display that is recessed into the working surface. The side view, which can be additionally provided in the aforementioned embodiment, clarifies the arrangement of the surgical instrument in the cleaning basket. The instructions become clearer, and the use of the reprocessing apparatus becomes more certain for the user.

The flat display can be configured as a screen, in particular a flat screen, and further in particular a 3D screen or a holographic display. An LCD display, a projector, e.g. a video projector, a laser projector or a holographic projector can likewise be used.

A screen can be provided as the display like those generally known as computer screens or flat screen televisions. Furthermore, if a 3D screen is used to represent spatial image information, then appropriate eyeglasses, such as polarizing glasses, can also be provided. They allow the image information displayed on the associated 3D screen to be perceived spatially. A spatial, especially holographic, representation of the surgical instrument in the cleaning basket represents very intuitive and vivid instructions.

A protective glass can be recessed into the working surface of the loading station, wherein the protective glass shields the display from outside shock and liquids. The user assistance system according to this embodiment is robust and reliable. The working surface including the recessed protective glass can be wipe-disinfected.

The display device can be a transparent display, which is integrated into the loading station such that the cleaning basket can be or is arranged below the display.

Arranging the display device above or below the cleaning basket depends on the application. For surgical instruments that are heavily soiled, a transparent display can be arranged above the cleaning basket. When arranged below the cleaning basket, there is a risk that the display device could become soiled, which could reduce the quality of the image produced.

The display device can be a projector that is integrated into the loading station above a working surface where the cleaning basket is placed during a loading process, the projection direction of the projector being oriented toward the cleaning basket, in that image information generated by the projector can be or is projected into the cleaning basket from an upper side that is provided for the loading.

A projector permits to project the at least approximately realistic image of the at least one surgical instrument directly onto the corresponding surgical instrument so that a correct arrangement of the instrument in the cleaning basket is immediately visible. In other words, the surgical instrument that is to be arranged does not cover up the graphical representation, which simplifies the handling of said instrument.

The control unit can be configured to use the display to reproduce dynamic and photorealistic image information relating to the process of arranging the at least one surgical instrument in the cleaning basket.

The representation of dynamic instructions can make it easier to understand the work steps that are to be carried out. The user thus receives instructions that are even easier to comprehend.

The user assistance system can comprise a camera or a comparable image capturing system that records at least the cleaning basket and optionally also a surrounding region and that is coupled with the control unit. The control unit is configured, for example, to identify the loading state of the cleaning basket or a movement of the user's hands during the loading process. Proceeding from this information, the graphical representation is adapted to the current loading state or respectively the progress of the loading process. For instance, it is possible for the dynamic graphical representation illustrating the loading state of the cleaning basket to be adapted to its speed in accordance with the actual loading state or respectively loading process of the cleaning basket. Likewise, individual steps of the loading process can be displayed again if it is determined that they have not been executed correctly. In this way, the operating safety of the user assistance system can be improved, and the system can additionally be flexibly adapted to the individual requirements of the user. Furthermore, the object can be solved by a reprocessing apparatus with at least one cleaning basket, a loading station and a user assistance system according to one or more of the aforementioned aspects. Moreover, the object can be solved by a medical workstation comprising a reprocessing apparatus according to one or more of the aforementioned aspects.

The same or similar advantages apply to the reprocessing apparatus and the medical workstation, as has already been mentioned with regard to the user assistance system, and so they will not be discussed again.

The object can also be solved by a method for cleaning and disinfecting a surgical instrument in a reprocessing apparatus, the at least one surgical instrument being arranged in a cleaning basket during the reprocessing, the method comprising:

arranging a cleaning basket on one side of an electronically controlled display device during the loading of the cleaning basket, the display device being integrated in a loading station, displaying a predetermined arrangement of the surgical instrument to be reprocessed in the reprocessing basket in its actual size and position, arranging the surgical instrument in the reprocessing basket, and performing a reprocessing of the surgical instrument.

The same or similar aspects and advantages apply to the method for cleaning and disinfecting the surgical instrument, as has already been mentioned with regard to the user assistance system.

The display device can be a flat display that is integrated into the working surface of the loading station, and the working surface can be configured for placement of the cleaning basket during a loading process, a first and a second flat display furthermore being comprised, and first image information that relates to a top view in the direction of the first display being displayed on the first display and second image information that relates to a side view in the direction of the second display being displayed on the second display.

Dynamic and photorealistic image information can be reproduced which is related to the process of arranging the surgical instrument in the cleaning basket by means of the display device.

3D image data, such as stereoscopic image data or holographic image data, can be reproduced by the at least one display device.

Finally, the object can be solved by a computer program product that, in accordance with one or more of the aforementioned aspects, prompts a user assistance system to perform a method in accordance with one or more of the aforementioned embodiments.

The same or similar aspects or advantages also apply to the method and the computer program product, as has already been mentioned with regard to the user assistance system.

BRIEF DESCRIPTION OF THE DRAWINGS

Further features will become clear from the description of embodiments together with the claims and the accompanying drawings. Embodiments can encompass individual features or a combination of multiple features.

The embodiments will be described below, without restricting the general intent of the invention, based on exemplary embodiments with reference to the drawings, whereby express reference is made to the drawings with regard to the disclosure of all details that are not explained in greater detail in the text. Wherein.

In the drawings, the same or similar elements and/or parts are provided with the same reference numbers in order to prevent the item from needing to be reintroduced.

DETAILED DESCRIPTION

Figure 1:
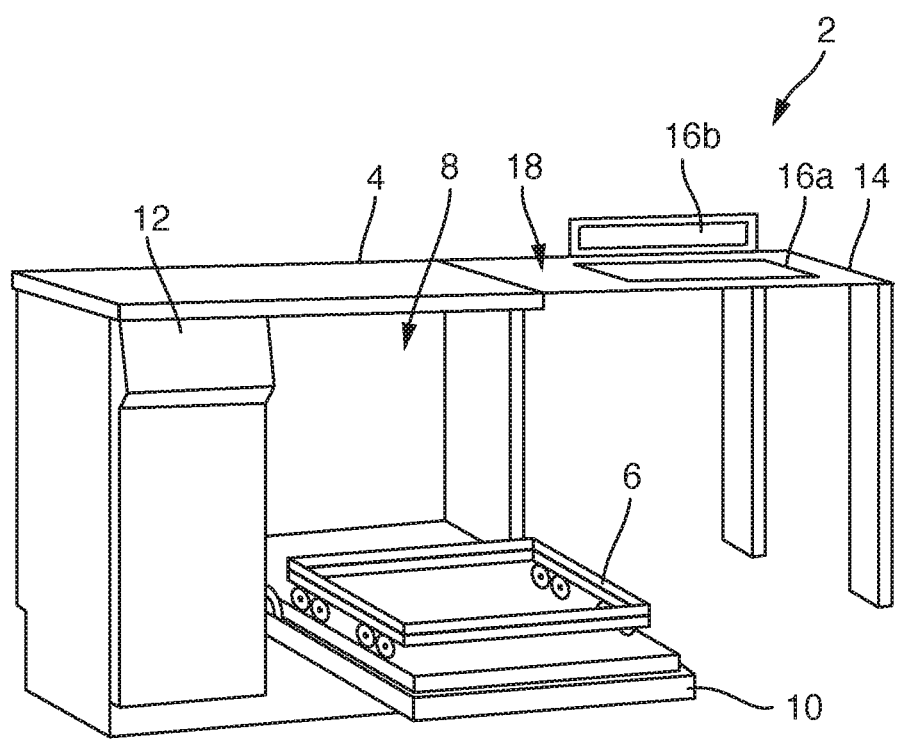
FIG. 1 illustrates a medical workstation comprising a reprocessing apparatus with a user assistance system in a schematic, simplified and perspective view.

FIG. 1 illustrates a schematic, simplified and perspective view of a medical workstation 2 comprising a reprocessing apparatus 4. Said apparatus comprises a cleaning basket 6, which is configured to receive at least one surgical instrument, such as an endoscope, a clamp, forceps or the like. A preparation process of cleaning and disinfecting takes place in an interior 8 of the reprocessing apparatus 4. The interior 8 is closed by a door 10 on the front side of the reprocessing apparatus 4. The reprocessing apparatus 4 is operated by means of an operating unit 12, for example.

To ensure a safe and reliable preparation of the surgical instruments in accordance with guidelines, it is important for them to be inserted correctly into the cleaning basket 6 and, if appropriate, to be connected to the provided connectors. The user of the reprocessing apparatus 4 is supported during the insertion of the surgical instrument or the surgical instruments into the cleaning basket 6. The present loading station 14 next to the reprocessing apparatus 4 has a user assistance system for this purpose.

Figure 2:
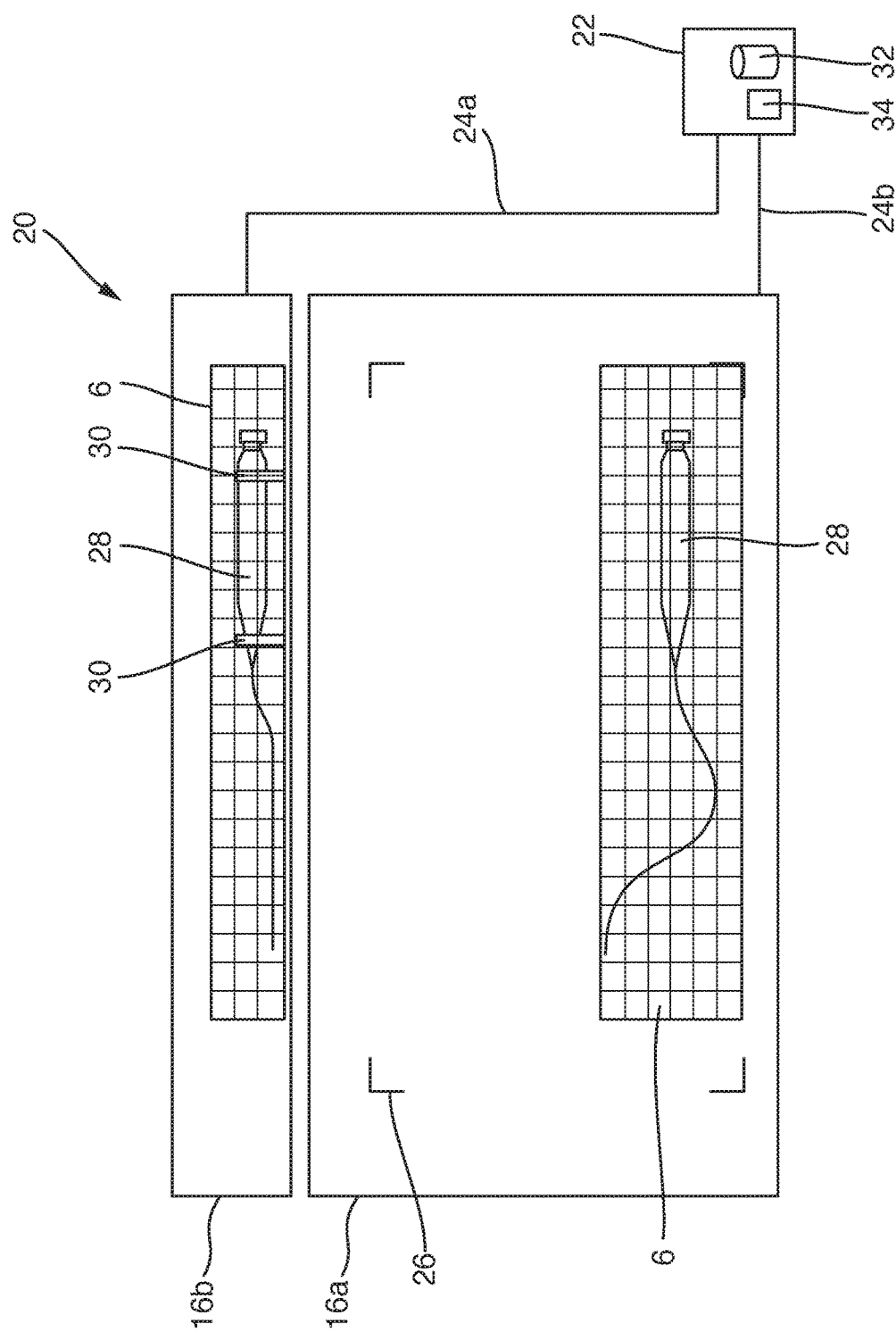
FIGS. 2-4 illustrate various user assistance systems in a schematically simplified view.

FIG. 2 illustrates a user assistance system 20 in a schematically simplified view. It comprises at least one electronically controlled display device and, in the exemplary embodiment shown here, a first flat display 16a and a second flat display 16b. The loading station 14 (cf. FIG. 1) comprises a working surface 18 for the placement of the cleaning basket 6 during the loading process. The first display 16a, which is e.g. a flat screen, is integrated into this working surface 18. The cleaning basket 6 is placed immediately above an active side of the first display 16a while it is loaded with the surgical instrument 28. A protective glass, which shields the display screen beneath it from shock and liquids in its surroundings, is preferably recessed into the working surface 18 of the loading station 14, especially the upper side of the working surface 18. The protective glass can be wipe-disinfected.

The second flat display 16b is located in a rear part of the loading station 14. Its active side faces toward the first display 16a. If the cleaning basket 6 is placed on the first display 16a, the active side of the second display 16b faces toward the cleaning basket 6. The active side of the first display 16a and the active side of the second display 16b enclose an angle of at least approximately 90°.

In order to aid the user in inserting the surgical instrument 28, such as an endoscope, into the cleaning basket 6, the first and second displays 16a, 16b are controlled such that image information is displayed in the actual size and position, which indicates a predetermined arrangement within the reprocessing basket 6 of the surgical instrument that is to be reprocessed. This is exemplified in FIG. 2.

For the sake of clarity, the first display 16a and the second display 16b are shown next to each other in one plane in FIG. 2. While a top view is displayed on the first display 16a, the second display 16b displays a side view. The user is given intuitive instructions as to how to insert the pictured endoscope into the cleaning basket 6. In addition to the displays 16a, 16b, the user assistance system 20 comprises a control unit (controller) 22, which is coupled with it so as to control the first and second displays 16a, 16b. Suitable connection lines 24a, 24b are provided for this purpose. The cleaning basket 6, which is likewise shown in a top view on the first display 16a and in a side view on the second display 16b, is positioned within the markings 26, one of which has been given a reference sign as an example. The surgical instrument 28, the endoscope in the exemplary embodiment shown here, is displayed realistically in its size and position on the displays 16a, 16b. The image information can be a photorealistic image.

The user is given an intuitive and simple visual representation of what position and in what way the surgical instrument 28 is to be placed in the cleaning basket 6. The top view displayed on the first display 16a and the side view displayed on the second display 16b complement each other in this context. For instance, it is possible to see on the second display 16b how the imaged endoscope is inserted into the mount 30 in the cleaning basket 6 and, if necessary, is attached to the provided adapter.

The control unit 22 of the user assistance system 20 has a memory containing a database 32, in which are stored the configurations in which the surgical instruments 28 can be inserted into the cleaning basket 6. For example, the database comprises all configurations of all surgical instruments that can be employed in a particular institution, such as a hospital.

It is necessary only to detect the type of surgical instrument 28 and optionally the type of cleaning basket 6, and the control unit 22 then provides the associated image information on the displays 16a, 16b. For this purpose, the control unit 22 also has a central processing unit (CPU) 34. To identify them, the surgical instrument 28 and optionally the cleaning basket 6 have machine-readable identifiers, such as a RFID tag, a bar code, a UDI code or a QR code.

The user assistance system 20 can be configured to represent dynamic, such as photorealistic, image information on the displays 16a, 16b. This information s relates to the process of arranging the surgical instrument 28 in the cleaning basket 6. In other words, a film or a moving video representation illustrating the process of inserting the surgical instrument 28 into the cleaning basket 6 can be reproduced on the displays 16a, 16b.

The user assistance system 20 can further comprise a camera or another suitable image capturing system, which is not shown here, with which the cleaning basket 6 and optionally also the surroundings of the cleaning basket 6 can be recorded. The control unit 22 is then configured to evaluate the recorded image information and determine, for example, a loading state of the cleaning basket 6. Likewise, a movement of the user's hands can be identified and analyzed. As a result, it can be determined whether the at least one surgical instrument 28 is or has been inserted into the cleaning basket 6 correctly and how far the process of inserting it into the cleaning basket 6 has progressed. It becomes possible in this way, for example, to adapt the speed of a video representation to the speed at which the user is able to arrange the surgical instrument 28 in the cleaning basket 6. Moreover, an incorrect loading of the cleaning basket 6 can be detected and the user can be prompted to correct the situation, possibly by means of a warning message. It is likewise provided that particular sequences of the process of handling the surgical instrument 28 are repeated during the process of inserting it into the cleaning basket 6.

The display or displays 16a, 16b can be a screen, such as a flat screen. An active side of the display 16a, 16b is that side on which the image information is reproduced. A flat screen can be used, such as those known from entertainment electronics or as computer screens. Furthermore, the display or displays 16a, 16b can be a 3D screen. This type of screen can be configured to display pairs of stereoscopic images that can be viewed by the user with a suitable aid, such as a pair polarizing 3D glasses. A 3D image can improve the intuitive representation of the process of inserting the surgical instrument 28, since, in addition to the image information, depth information relating to the position of the surgical instrument 28 is displayed. This also applies to the case according to a further exemplary embodiment, in which the display 16a, 16b is a holographic display.

Figure 3:
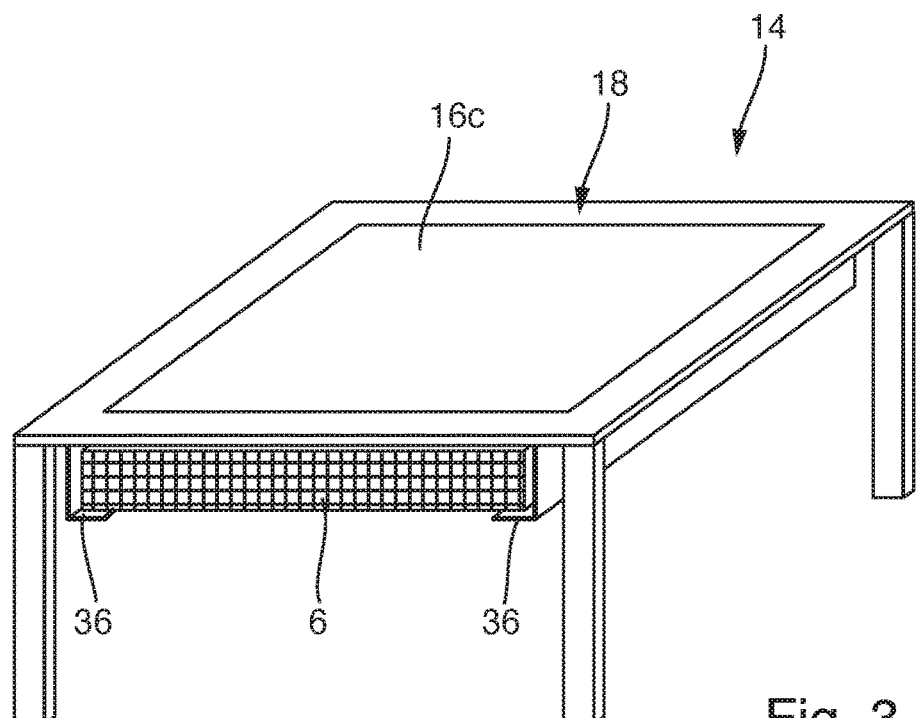

FIG. 3 shows a simplified schematic perspective view of a loading station 14, such as a table, that has a transparent display 16c recessed into its working surface 18. This is integrated into the loading station 14 in such a way that the cleaning basket 6 is or can be arranged below the display 16c. For this purpose, appropriate mounting brackets 36 are located on the lower side of the working surface 18. A free space between an upper edge of the cleaning basket 6 and a lower side of the working surface 18 is selected to be large enough that a user is capable of comfortably reaching his or her hands into this intermediate space and arranging a surgical instrument 28 in the cleaning basket 6.

During insertion of the surgical instrument(s), the user matches the e.g. photorealistic representation of the instruments on the transparent display 16c with the instruments visible below it. The displayed arrangement of the surgical instruments 28 in the cleaning basket 6 can be optimized with regard to the efficiency of the reprocessing apparatus 4 by the user assistance system. Thus it can display how an optimal number of surgical instruments 28 should be arranged in the cleaning basket 6, with the hygienic requirements being optimally satisfied while a maximum number of surgical instruments 28 are reprocessed in a single cleaning process. Naturally, this range of functions applies to all of the exemplary embodiments.

Figure 4:
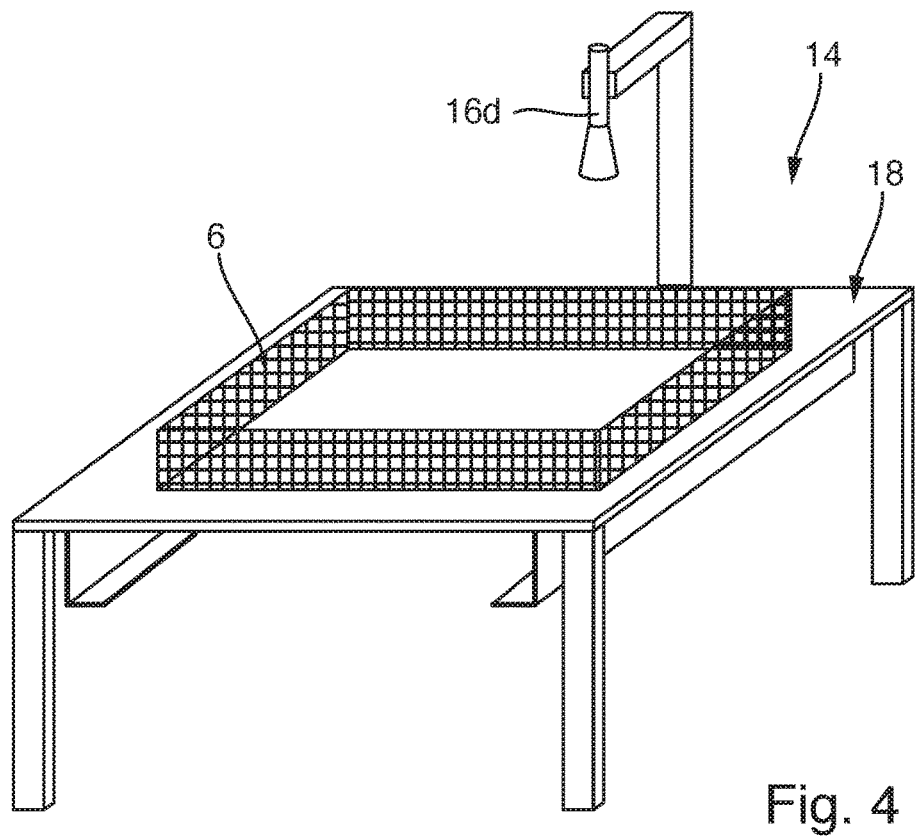

FIG. 4 shows a further schematic and perspective view of a loading station 14, which has a projector 16d as the display device. A cleaning basket 6 is arranged on a working surface 18. The cleaning basket 6 is placed there during the loading process. The projector 16d projects in a direction toward the cleaning basket 6. In this way, image information indicating the arrangement of the surgical instruments 28 in the cleaning basket 6 can be projected into the cleaning basket 6 by means of the projector 16d. If the image or the outline of a surgical instrument 28 is projected directly onto the surgical instrument itself, then a user can assume that he or she has arranged the instrument properly in the cleaning basket 6.

In one method for cleaning and disinfecting a surgical instrument 28 in the reprocessing apparatus 4, the cleaning basket 6 is arranged e.g. on the upper side of the first display 16a (FIG. 1). The predetermined arrangement of the surgical instrument 28 to be reprocessed in the reprocessing basket 6 is then represented in its actual size and position on this display 16a. The user arranges the surgical instrument 28 in the reprocessing basket 6 and introduces it into the interior 8 of the reprocessing apparatus 4 to perform the preparation process.

The same procedure can also be carried out in the apparatuses shown in FIGS. 3 and 4, the difference being that the cleaning basket 6 is arranged below a transparent display 16c (FIG. 3) or that an image is projected into the cleaning basket 6 from the upper side (FIG. 4).

To represent the image information on the display(s) 16a, 16b, a computer program product is also provided, which enables the user assistance system 20 to carry out the method. The corresponding computer program product can be provided in the database 32 and is executed by the central processing unit 34 of the control unit 22.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

2 Medical workstation
4 Reprocessing apparatus
6 Cleaning basket
8 Interior
10 Door
12 Operating unit
14 Loading station
16a, 16b Flat display
16c Transparent display
16d Projector
18 Working surface
20 User assistance system
22 Control unit
24a, 24b Connecting lines
26 Marking
28 Surgical instrument
30 Mount
32 Database
34 Central processing unit
36 Mounting bracket

What is claimed is:

1. A user assistance system of a reprocessing apparatus for cleaning and disinfecting at least one surgical instrument arranged in a cleaning basket, the user assistance system comprising:

at least one electronically controlled display device, the at least one electronically controlled display device being integrated in a loading station and being configured for arranging the cleaning basket on one side of the display device during loading of the cleaning basket; and a controller coupled with the at least one electronically controlled display device, the controller being configured to control the display device such that an image of the surgical instrument is displayed in an actual size and position which indicates a predetermined arrangement within the cleaning basket of the surgical instrument that is to be reprocessed;

wherein the image is displayed on a working surface of the loading station, the working surface being configured for the placement of the cleaning basket during a loading process of the surgical instrument in the cleaning basket; and the at least one electronically controlled display device comprises a first flat display and a second flat display, each of the first and second flat displays being coupled to the control unit, the controller being configured to display, on the first flat display, first image information that relates to a top view in a direction of the first flat display and, on the second display, second image information that relates to a side view in a direction of the second flat display.

2. The user assistance system according to claim 1, wherein the first flat display and the second flat display are positioned at an angle of at least 90° relative to each other.

3. The user assistance system according to claim 1, wherein the at least one electronically controlled display device is one of a flat screen, a 3D screen or a holographic display.

4. The user assistance system according to claim 1, further comprising a protective glass recessed into the working surface of the loading station, wherein the protective glass shields the at least one electronically controlled display device from shock and liquids.

5. The user assistance system according to claim 1, wherein the at least one electronically controlled display device is a transparent display, the transparent display being integrated into the loading station in that the cleaning basket is arranged below the transparent display.

6. The user assistance system according to claim 1, wherein the at least one electronically controlled display device is a projector integrated into the loading station above a working surface where the cleaning basket is placed during a loading process, a projection direction of the projector being oriented towards the cleaning basket, image information generated by the projector is projected into the cleaning basket from a side of the cleaning basket that is provided for loading of the at least one surgical instrument.

7. The user assistance system according to claim 1, wherein the controller is configured to use the at least one electronically controlled display device to reproduce dynamic and photorealistic image information for assisting a user in arranging the at least one surgical instrument in the cleaning basket.

8. A reprocessing apparatus comprising:
the user assistance system according to claim 1,
the cleaning basket, and
he loading station.

9. A medical workstation comprising the reprocessing apparatus according to claim 8.

10. A method for cleaning and disinfecting at least one surgical instrument in a reprocessing apparatus, the at least one surgical instrument being arranged in a cleaning basket during reprocessing, the method comprising:

arranging the cleaning basket on one side of an electronically controlled display device during the loading of the cleaning basket, the electronically controlled display device being integrated in a loading station, displaying an image of the at least one surgical instrument having a predetermined arrangement of the at least one surgical instrument to be reprocessed in the cleaning basket in an actual size and position of the at least one surgical instrument, arranging the at least one surgical instrument in the cleaning basket according to the display, and performing a reprocessing of the surgical instrument, wherein the displaying displays an image on a working surface of a loading station and the arranging comprises placing the cleaning basket on the working surface during the loading process of the surgical instrument in the cleaning basket; and the electronically controlled display device comprises first and second flat displays, wherein the displaying comprises displaying first image information that relates to a top view in a direction of the first flat display on the first flat display and displaying second image information that relates to a side view in a direction of the second flat display on the second flat display.

11. The method according to claim 10, wherein the displaying comprises displaying dynamic and photorealistic image information for arranging the at least one surgical instrument in the cleaning basket on the electronically controlled display device.

12. The method according to claim 10, wherein the displaying comprises displaying one of 3D image data, stereoscopic image data or holographic image data on the electronically controlled display device.

13. A computer-readable storage device storing instructions that cause a computer to perform, for cleaning and disinfecting at least one surgical instrument in a reprocessing apparatus where the at least one surgical instrument being arranged in a cleaning basket during reprocessing:

arranging the cleaning basket on one side of an electronically controlled display device during the loading of the cleaning basket, the electronically controlled display device being integrated in a loading station, displaying an image of the at least one surgical instrument having a predetermined arrangement of the at least one surgical instrument to be reprocessed in the cleaning basket in an actual size and position of the at least one surgical instrument arranging the at least one surgical instrument in the cleaning basket according to the display, and performing a reprocessing of the surgical instrument, wherein the displaying displays an image on a working surface of a loading station and the arranging comprises placing the cleaning basket on the working surface during the loading process of the surgical instrument in the cleaning basket; and the electronically controlled display device comprises first and second flat displays, wherein the displaying comprises displaying first image information that relates to a top view in a direction of the first flat display on the first flat display and displaying second image information that relates to a side view in a direction of the second flat display on the second flat display.

* * * * *